United States Patent [19]

Geho et al.

[11] Patent Number: 4,740,375

[45] Date of Patent: Apr. 26, 1988

[54] GELCORES

[75] Inventors: W. Blair Geho; John R. Lau, both of Wooster, Ohio

[73] Assignee: Technology Unlimited, Inc., Wooster, Ohio

[21] Appl. No.: 705,023

[22] Filed: Feb. 25, 1985

[51] Int. Cl.$^4$ ................................................ A61K 9/50
[52] U.S. Cl. ...................... 424/450; 424/456; 424/460; 514/801; 514/963; 514/965
[58] Field of Search .............. 424/38, 450, 456, 460; 514/801, 965, 963; 252/316

[56] References Cited

U.S. PATENT DOCUMENTS

| | | | |
|---|---|---|---|
| 4,230,687 | 10/1980 | Sair et al. | 514/965 |
| 4,310,505 | 1/1982 | Baldeschwieler et al. | 252/316 |
| 4,331,654 | 5/1982 | Morris | 424/450 |
| 4,356,167 | 10/1982 | Kelly | 252/316 |
| 4,377,567 | 3/1983 | Geho | 424/85 |
| 4,501,728 | 2/1985 | Geho et al. | 424/38 |
| 4,587,267 | 5/1986 | Drake et al. | 514/965 |
| 4,603,044 | 7/1986 | Blair et al. | 424/38 |
| 4,619,794 | 10/1986 | Hauser | 424/38 |
| 4,622,244 | 11/1986 | Lapka et al. | 514/963 |

*Primary Examiner*—Ronald W. Griffin
*Attorney, Agent, or Firm*—Frijouf, Rust & Pyle

[57] ABSTRACT

This disclosure recognizes the fact that the technology of making vesicles from lecithin and lecithin-like molecules, although well known and highly developed, is associated with problems of instability. It is known that vesicles coalesce, rupture and spill their contents long before the vesicle is used for its intended purpose.

It has been discovered and disclosed herein that the deterioration of the vesicle delivery system is due in part to the rupture of the bipolar lipid vesicle membrane by the contents of the core volume or by an external agent. For example, the more detergent-like the properties of the pharmacological agent within the vesicle core volume, the more pronounced will be the attack on the vesicle wall interior. These events in turn will lead to vesicle membrane rupture.

This disclosure sets forth the proper manufacturing techniques to achieve vesicle stability following the discovery and also discloses a large-scale experiment which fully establishes the function taking place microscopically in the true vesicle. The experiment designed to substantiate the discovery is one using visible sized dialysis bags to show that gelatinized pharmacological agents are capable of existing without disruption in the appropriate solutions. The dialysis bag could not be used in the administration of a pharmacological agent to a person but illustrates on a large-scale what takes place microscopically in the actual vesicle environment.

3 Claims, 1 Drawing Sheet

GELCORES

BACKGROUND OF THE INVENTION

Prior Art

Many disease states encountered in humans and animals are difficult to correct by drug administration, regardless of whether the drug is delivered orally or parenterally. This problem is often due to the fact that the drug cannot reach the appropriate site of action or that it exhibits unacceptable side effects.

Bipolar lipid vesicles are a known and relatively new biochemical approach being intensely studied as possible carriers of drugs, hormones, nutrients and pharmacological agents.

Bipolar lipid vesicles are synthesized by sonicating ampholiphilic long-chain lipid compounds such as distearoyl lecithin. The sonication process produces high frequency sound waves and initiates a reaction sequence which causes the lipid chains to fragment. The dispersed lipid then assumes a spherical shape which has a greater thermodynamic stability than individual fragments. During the formation of the spherical vesicle, some of the pharmacological agent is captured and internalized within the vesicle core volume.

Some vesicles are intended to circulate in the blood stream and designed to slowly release their core volume contents in order to provide a sustained release of drug over an extended period of time.

Other vesicles are supplied with target molecules which are recognized by selected tissues and cell types. In this way, the hormone insulin, for example, may be delivered to the liver. See Geho, U.S. Pat. No. 4,377,567, issued on Mar. 22, 1983.

One persistent problem associated with vesicle technology has been very short vesicle shelf life, which necessitates manufacturing vesicles very soon before their use and in relatively small quantities. This type of special manufacture is prohibitively expensive. Some preparations have reported shelf lives on the order of several months, but most experience has indicated that vesicles exhibit a shelf life that is measured in weeks. A short vesicle shelf life inhibits wide-scale manufacture and distribution, thereby limiting the use of vesicles to special situations and small-scale research applications.

Vesicle instability has two important features: first, vesicles lose their structural integrity with time; and secondly, the structural lesions result in the leaking of the core volume content to the external media. Once the contents of the vesicle core volume are leaked to the external media, they can no longer be targeted.

After manufacture, vesicles are suspended in a buffer solution that has the appropriate physiological pH and ionic strength to effectively ionize the charged functional groups. Vesicles may be negatively or positively charged depending upon the type of charged ampholiphilic materials incorporated into the vesicle membrane. Examples of negatively and positively charged lipids are dicetyl-phosphate and stearylamine. As a consequence of membrane incorporation of charge groups, an ion atmosphere is developed which results in a charge-charge repulsion between neighboring vesicles that contribute to their short term stability. However, after a period of time ranging from a few weeks to several months, the charge-charge repulsion becomes neutralized, and the vesicles begin to aggregate and eventually fuse. From a morphological point-of-view, the vesicles are undergoing transformation from a colloid dispersion to a coarse suspension.

When fusion occurs, the lipid membrane structures deteriorate rapidly, and the vesicles lose their core volume constituents. The deteriorated membranes coalesce and aggregate on the bottom of the storage vial. As a result of this sequence of events, the vesicle preparation is unsuitable for further use.

DEFINITIONS

For economy of communication, the vesicles with stabilized content in the core volume thereof will be referred to hereinafter as "gelcores." The intent of this invention is to substantially immobilize, or at least greatly retard, the molecular movement of the pharmacological agent which would otherwise interact with the vesicle membrane and cause the early deterioration of the vesicle. An additional intent is to inhibit the pharmacological agent from interacting in an autocatalytic fashion leading to a loss in chemical or biological activity. Further degradation of an internalized pharmacological agent may occur as a result of hydrolytic activity initiated by the solvent or aqueous phase either within the vesicle core volume or in the continuous media. In contrast, if the vesicle membrane of a gelcore becomes damaged as a result of an action on the exterior surface of the vesicle membrane, the core volume contents being entrapped in a gel matrix will be prevented from leaking because they are immobilized.

"Pharmacological agent" will be used hereinafter in a broad generic sense to indicate any content within the vesicle which is intended for administration to a warm-blooded animal (i.e., a human). It is not the intention of this invention to administer a particular type of chemical substance to the warm-blooded animal, but rather the intention is to improve the administration of any material, whether that administration is oral or parental.

"Gel." There is a large number of animal, vegetable and mineral substances which will structure water. These materials are well known in the food industry and are widely used in medical practice.

Doxorubicin hydrochloride will be abbreviated to Dxn.

OBJECTS OF THE INVENTION

It is an object of this invention to structure the aqueous phase of the vesicle core volume, thereby creating a gelcore which will retard or inhibit the migration of pharmacological agents to the bipolar wall of a vesicle. The result is to prevent or greatly lessen vesicle wall deterioration from the interior of the vesicle.

It is a further object of this invention to create a new delivery system wherein pharmacological agents within the vesicle core volume may retain their original level of chemical or biological activity even though some of the vesicle walls are ruptured. The rupturing could be initiated by an agent external to the vesicle membrane in the continuous media.

It is a still further object of the invention to provide vesicle core volume structures which will remain stable, facilitating shelf life stability.

In addition, it is a further object of the invention to inhibit or retard the pharmacological agent from losing chemical or biological activity as a result of an autocatalytic event.

It is also an object of the invention to inhibit any hydrolytic or untoward action of the aqueous phase within the vesicle core volume on the pharmacological agent.

It is a further object of this invention to inhibit any hydrolytic or untoward action of the external aqueous phase on the constituents of a gelcore should the gelcore become exposed to the external aqueous media due to an opening or lesion in the vesicle membrane.

DESCRIPTION OF THE PREFERRED EMBODIMENT

Figure 1:
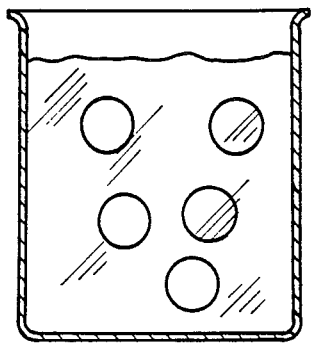
FIG. 1 illustrates a container with vesicles which have been formed with solubalized gelatin in the sol state in the core volume, as well as in the external media.
Figure 2:
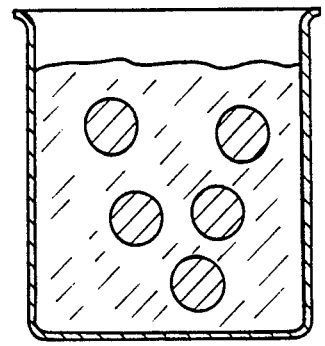
FIG. 2 depicts a container wherein the material within the container is an external media which has been diluted at a temperature that is above the gel-to-sol transition temperature in order to prevent the gelatin in the external media from setting. The concentration of gelatin sol in the vesicle core volume remains the same as in FIG. 1.
Figure 3:
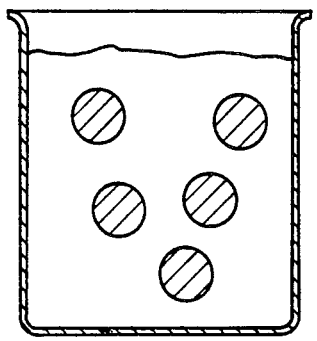
FIG. 3 depicts a container wherein the external media within the container has been removed by gel filtration chromatography and replaced by an appropriate buffer. This step does not have to be preformed at a temperature that is above the gel to sol transition temperature. The concentration of gelatin in the vesicle core volume remains the same as in FIGS. 1 and 2.
Figure 4:
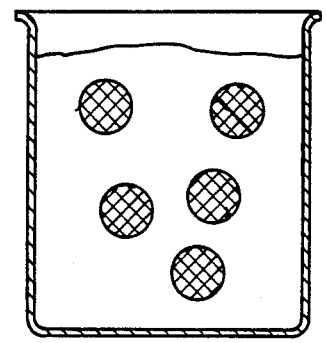
FIG. 4 illustrates a container with external media buffer wherein the temperature of the vesicle preparation is gradually lowered which results in a transition of the gelatin from the sol state to the gel state. Diagrammatically this process is illustrated by depicting the core volume with a cross-hatched pattern. Gel cores have been formed.
Figure 5:
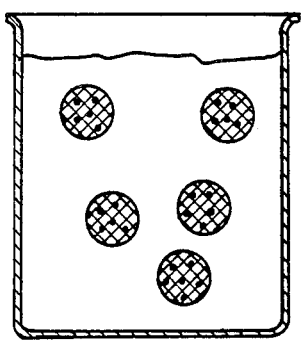
FIG. 5 illustrates the gelcores depicted by a cross-hatch pattern which has immobilized the entrapped core volume constituent indicated by dots. This illustration shows gelatins and the entrapped constituents have been stabilized.
Figure 6:
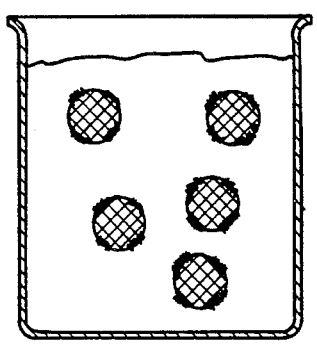
FIG. 6 depicts the vesicle membranes which surround the gelcores beginning to loose structural integrity and develope lesions. This event could be initiated by a vesicle-to-vesicle interaction or vesicle interaction with a storage vial. The gelcores and the entrapped consitutents are still intact and stabile.
Figure 7:
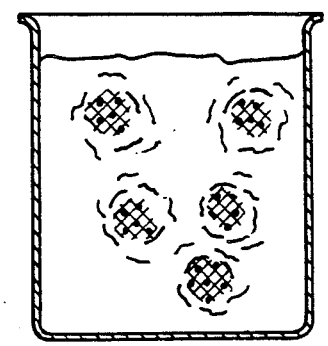
FIG. 7 shows that the continued disruption of the vesicle membrane is occurring. Membrane fragments are observed floating in the external media, but the gelcores and the entrapped constituents are still intact and stable. Some of the vesicle membrane remains for targeting purposes.

The description of this invention address some of the essential features of gelcores, which not only offer new drug delivery capbility, but also impart various stabilizing properties to the entire drug delivery system. Gelcores have properties and exhibit benefits in drug dosing and delivery that surpass those of traditional vesicles. Therefore, the concept "gelcores" should be viewed in the context of a unique and new delivery system that possesses inherent stabilizing properties.

The beneficial properties of gelcores are numerous, and one experimental use will be set forth herein. A paper has been published by Forssen and Tokes of the School of Pharmacy and Department of Biochemistry at the University of Southern California in *Procedures, National Academy of Sciences, U.S.A.*, Volume 78, number 3, pp. 1873–1877, March, 1981. In the Forssen and Tokes publication, the molecule doxorubicin hydrochloride (Dxn) is described as an anthracycline antibiotic with potent activity against a wide variety of human neoplasms.

It is known that the native molecule of Dxn in an unprotected state has had limited use in man, due to its pronounced cardiotoxicity. The Forssen and Tokes study has shown that if Dxn is incorporated into the core volume of vesicles or liposomes, not only was the incidence of cardio-toxicity reduced, but the chemotherapeutic potential against two murine leukemias, referred to as L-1210 and P-388, was increased. These pharmacological effects resulted in an increased therapeutic index when Dxn was used in conjunction with lipid vesicles.

It is known that vesicle walls deteriorate with time and allow leakage of their core volume. This is one of the aspects that is addressed by this invention, but in the Forssen and Tokes study, the leaking vesicle was the means employed to allow the slow release of the highly cardiotoxic Dxn. By utilizing this slow release phenomenon, the pharmacological agent was not as traumatic to the heart muscle as was the native Dxn molecule when injected without the protective vesicle membrane.

The purpose of the foregoing discussion, with respect to the published knowledge concerning Dxn entrapped within vesicles, is to set forth the basis for the testing and proof of the present invention. This invention is demonstrated by the pharmacological agent Dxn, and is applicable to the delivery of any pharmacological agent.

The object, as set forth above, has indicated that the intent of this invention is to produce a core volume which will keep its integrity even though the vesicle wall may develop lesions as a result of an interaction by an internal or external agent. It is the intention of this invention to prevent any release of the core volume in the event of a lesion or actual rupture of the vesicle wall and in a concomitant manner prevent hydrolysis or autocatalytic degradation of the agent itself. The reference to the prior study by Forssen and Tokes is to show that Dxn has detergent-like properties which can disrupt the walls of the vesicle. If that material, known to be disruptive of the vesicle wall, can be successfully incorporated into a core volume and be shown not to leak or be altered in any manner within the carrier, even though the vesicle is ruptured, then the objects and purpose of this invention will be proven.

Therefore, to restate, it has been seen that upon incorporation of Dxn in the vesicle core volume, the detergent-like ability of Dxn facilitated the disruption of the vesicle membrane, which led to spillage or leakage of Dxn from the vesicle core volume into the external media. These events represent unacceptable consequences resulting from the interaction of Dxn with the vesicle membrane.

The structure of Dxn is shown below:

[Chemical structure diagram of doxorubicin-like molecule with OCH₃, OH, O, COCH₂OH, CH₃, NH₂ substituents]

Bearing in mind that the use of Dxn molecule is a means of proving this invention, it is then noted that the Dxn molecule has an ampholiphilic nature, and therefore, a lipid-like portion which seeks, or migrates, to the lipid-like or hydrophobic regions of the vesicle membrane with an accompanying interaction that is deleterious to the structural integrity of the vesicle wall. It is the purpose of this illustration to disclose a means by which the detergent-like ability of Dxn, in addition to a broad spectrum of other pharmacologically active compounds, can be significantly circumvented in a novel fashion, thus resulting in a new drug delivery system.

This invention embodies two separate functions for the shelf life enhancement of the vesicles. First, the vesicle core volume is stabilized to slow or retard the availability of the core volume to the vesicle wall. Second, the core volume constituents are stabilized in regard to autocatalysis, as well as aqueous phase hydrolysis.

The principal of internal stabilization will be understood by the following example:

Vesicle membranes are stabilized against Dxn ampholiphilic molecules and virtually any core volume constituent by entrapping the active ingredient in a gel-like matrix using vegetable, animal or mineral gel material.

The means of producing vesicles is now a known art. However, a recently developed and reliable method is disclosed in U.S. application Ser. No. 606,714, filed May 3, 1984, and entitled *Hepatocyte Directed Vesicle Delivery System*.

Essentially, the vesicles are formed as illustrated by a batch in which:

L-α-Distearoyl lecithin (DSL),
Dicetyl Phosphate (DCP) and
Cholesterol (CHOL)

are properly mixed together and then sonicated and annealed for a given period of time.

The above listing is a specific batch example in the above-referenced pending application. It is only one example of a means of forming vesicle membranes. The literature contains many specific examples which may be employed.

According to this invention, vegetable gelatin obtained from Sigma Chemical Company, St. Louis, Mo. 63178 (i.e., Gelatin, Vegetable, Type 1), was supplied at concentrations of from 0.1 to 50 mg/ml as a sol. The sol state was maintained by elevating the temperature to approximately 60° C.

According to the literature, Dxn will destroy the vesicle wall and leak from the vesicle. If the disruptive action of Dxn can be essentially prevented, or materially slowed, then this invention will solve the perplexing problem of how to achieve useful shelf life stability in regard to vesicle manufacture and storage with any core volume.

PROCEDURE

As the vesicles are formed, they envelop the warm, fluid sol of which solubilized gelatin is an example. The constituents of the vesicle core volume then are composed of buffer, Dxn and gelatin in the fluid or sol state. Under vesicle manufacturing conditions, there is also sol in the external media (that is, the aqueous volume between the vesicles, also regarded as the continuous phase).

During the vesicle manufacturing process, the fluid sol located in the external media of the vesicle preparation is removed. The sol is diluted at an elevated temperature (i.e., 60° C. for DSL-DCP-CHOL vesicles, for example) to prevent the sol from setting and thus transforming in the gel state. Once gel inhibition by dilution has been accomplished in the external media, the vesicles are annealed and chromatographed, according to known technology, to remove the diluted sol. The consequence is depicted as shown in the drawings.

The dilution of the external sol prior to chromatography, as shown in the illustrations Supra, is employed according to this invention during the manufacturing process to prevent the sol from setting in the external media. The dilution is made while concomitantly maintaining a high concentration of the sol in the internal vesicle core volume.

As the temperature of the reaction mixture is lowered, the promotion of gelcore setting is enhanced. Once the gelcore is set, and the gel has structured water in conjunction with the entrapped constituents such as Dxn, the fluid dynamics of vesicle membrane interaction with the gelcore are greatly reduced because the molecular rotation of the entrapped constituents has been minimized. The stablization of all molecular constituents of the core volume will then be accomplished. The active pharmacological agent, such as Dxn, can no longer migrate into the hydrophobic regions of the vesicle membrane to effect a detergent-like membrane destabilization. This fact will be applicable to every drug or active pharmacological agent in which gelcore stabilization is utilized.

During the process of vesicle formation, the gelatin molecules will not be cross-linked or manifest the gel state but will demonstrate properties similar to those of freely circulating proteinaceous molecules. Since gelatin molecules are by nature predominantly hydrophilic and water soluble, they are readily excluded from the hydrophobic regions of the vesicle membrane during the sonication process.

Gelcores provide a means of internal core volume structuring that will contribute to the stabilization of the entire vesicle population to be used in drug dosage forms. The surface-to-surface interaction between traditionally manufactured vesicles, the result of which is ion-ion or ion-dipole promoted bonding, will not permanently inhibit the following sequence of events: aggregation, fusion and eventual leaking or spilling of core volume contents. These events are circumvented by using the principals set forth herein according to the discoveries of this invention.

While the electronic interaction between neighboring vesicles is not inhibited with the use of gelcores, the leaking of the vesicle contents is inhibited. Even a spuriously encountered membrane lesion would not facilitate leakage. This stability is due to the nature of water-structuring and mobility of the entrapped constituents. If vesicle aggregation, fusion and settling should occur with any gelcore preparation, these physical events will not effect the drug delivery capability of the vesicle dosage form. The gelatinous interior of the core volume provides vesicles with increased resilience. This property circumvents the destabilization phenomenon that has been observed in traditional vesicle preparations.

Secondly, the following example addresses a further dimension of the invention. It has been found that gelcores exhibit physical properties such as coefficients of expansion and contraction of the membrane constituents in lipid vesicles. In addition, the specific gravity or density of the gelcores closely resembles the density of the lipid constituents of the vesicle membrane. In both instances, similar physical properties will facilitate and enhance constituent compatibility, as well as stability.

The properties of gelcores described in the proceeding procedures are necessary in order to achieve optimum stabilization. However, if perfect stabilization is not obtained, this invention has a second function, in that the settling of gelcore suspension does not necessarily signify vesicle membrane destruction as observed with traditional prior art vesicle systems.

EXPERIMENT

Because a vesicle is too small for facile verification procedures, the following procedure will illustrate and confirm the concepts of the invention.

This invention has been conducted in the laboratory where various concentrations (i.e., 10 mg/5 ml, 20 mM Tris-HCL, pH 7.4; 15 mg/5 ml; and 20 mg/5 ml) of vegetable gelatin were solubilized by heating and then placed in dialysis bags. The dialysis bags, while still warm, contained gelatin in the sol state. The bubbles in the sol mixed readily. The bags were placed in a beaker of 60° C. buffer, 20 mM Tris-HCL, pH 7.4, with no preservative and then placed in the refrigerator at 5° C. Over a period of one hour, the contents of the dialysis bags formed a gel. The extent of gelatination proceeded most rapidly from the high concentrations of gelatin to the lower concentration of gelatin. When the dialysis bag was cut open, solidified gelatin was observed.

The experiment illustrates and confirms that a gel can be formed inside a semi-permeable membrane when placed in a buffer solution (i.e., 20 mM Tris-HCL at pH 7.4) with no preservative. This gel can be formed inside a semi-permeable membrane, even though there is a liquid medium external to the dialysis bag. Dynamic equilibrium of buffer moving in and out of the membrane has no effect on the sol-to gel transition. In addition, gel was not observed to expand or contract upon settling. Once dry gelatin has become hydrated, any increase in gel volume is insignificant in regard to its expansion against a semi-permeable membrane.

This experiment demonstrates on a large scale what takes place in the individual bipolar lipid membrane vesicles and confirms the ability to form gelcore structures within integral vesicle walls.

From a physical-chemical point-of-view, gels will have to be utilized that exhibit the appropriate sol-to-gel transition temperatures and still remain compatible with human dose forms. Various kinds of animal gelatins have been used as plasma-expanders in humans at relatively high concentrations for the treatment of shock. The small quantity of gel in gelcores, when administered during drug dosing, does not present a problem for the patient.

Experimentally it has been observed that vegetable gelatin particles less than 1 mm in diameter remain in the gel state while temporarily suspended in an aqueous 40 mM phosphate buffer, pH 7.4, at 5° C. The aforementioned reactions and physical events are governed by chemical equilibria.

What is claimed is:

1. A pharmacological vehicle made by the method of mixing a pharmacological agent and a gel-forming material in a sol state at a temperature above the sol-to-gel transition temperature of the gel-forming material;

mixing therewith a quantity of a lipid material characterized by the ability thereof to form bipolar lipid vesicles under sonication;

thereafter sonicating the mixture to create bipolar lipid vesicles with entrapped pharmacological agents and gel-forming sol in the core volume thereof; and thereafter processing the sol portion which is exterior to the formed vesicles to render said portion unavailable to form a set or structured state and with the vesicle core remaining unaffected.

2. A pharmacological vehicle comprising a bipolar lipid vesicle containing at least one pharmacological agent as a core volume stabilized by a gel-forming material to slow the availability of the core volume to autocatalysis or aqueous phase hydrolysis.

3. A composition of matter which is a vehicle for internal administration of a pharmacological substance to a human or animal, comprising:

(A) a first component which is a drug or diagnostic agent, said first compound being encapsulated in:

(B) a second component which comprises lipid membrane structures in the form of vesicles known to be compatible to the warm blooded animal system, and (C) a quantity of gel within said lipid membrane containing said first component as a physically entrapped pharmacological agent within said gel.

* * * * *